United States Patent [19]
Reich et al.

[11] Patent Number: 5,724,138
[45] Date of Patent: Mar. 3, 1998

[54] WAVELET ANALYSIS FOR LASER ULTRASONIC MEASUREMENT OF MATERIAL PROPERTIES

[75] Inventors: Judith E. Reich, Andover; Petros A. Kotidis, Framingham, both of Mass.

[73] Assignee: Textron Systems Corporation, Wilmington, Mass.

[21] Appl. No.: 634,286

[22] Filed: Apr. 18, 1996

[51] Int. Cl.$^6$ .................................................. G01B 9/02
[52] U.S. Cl. .................... 356/359; 356/345; 356/432 T
[58] Field of Search ........................ 356/345, 351, 356/357, 432 T, 349, 359, 360; 73/655

[56] References Cited

U.S. PATENT DOCUMENTS

| | | | |
|---|---|---|---|
| 3,601,490 | 8/1971 | Erickson | 356/106 |
| 3,694,088 | 9/1972 | Gallagher et al. | 356/106 |
| 4,372,163 | 2/1983 | Tittmann et al. | 73/602 |
| 4,521,118 | 6/1985 | Rosencwaig | 374/5 |
| 4,541,279 | 9/1985 | Schomberg | 73/597 |
| 4,541,280 | 9/1985 | Cielo et al. | 73/603 |
| 4,633,715 | 1/1987 | Monchalin | 73/657 |
| 4,639,669 | 1/1987 | Howard et al. | 324/239 |
| 4,658,648 | 4/1987 | Roddeck et al. | 73/597 |
| 4,659,224 | 4/1987 | Monchalin | 356/352 |
| 4,966,459 | 10/1990 | Monchalin | 356/358 |
| 5,035,144 | 7/1991 | Aussel | 73/602 |
| 5,061,071 | 10/1991 | Fujita et al. | 356/360 |
| 5,068,541 | 11/1991 | Kondo | 250/571 |
| 5,080,491 | 1/1992 | Monchalin et al. | 356/352 |
| 5,083,869 | 1/1992 | Nakata et al. | 356/432 |
| 5,402,233 | 3/1995 | Schultz et al. | 356/351 |
| 5,604,592 | 2/1997 | Kotidis et al. | 356/357 |

OTHER PUBLICATIONS

"Laser Generation of Convergent Acoustic Waves and Applications to Materials Evaluation", P. Cielo and C.K. Jen, 1986, IEEE, pp. 515–526 (no month available).

*Primary Examiner*—Frank G. Font
*Assistant Examiner*—Robert Kim
*Attorney, Agent, or Firm*—Perman & Green, LLP

[57] ABSTRACT

A laser ultrasonics technique is used to characterize a composite dispersive response signal from a sample under analysis, such as a semiconductor wafer. Rather than measuring individual acoustic wave velocities at specific frequencies, an entire dispersive response signal is analyzed. In a presently preferred embodiment of this invention the entire dispersive response signal is analyzed using a wavelet-based technique, such as a discrete wavelet transform analysis technique. The discrete wavelet transform analysis technique is shown to provide an accurate, non-contact measurement of the temperature of the wafer.

12 Claims, 9 Drawing Sheets

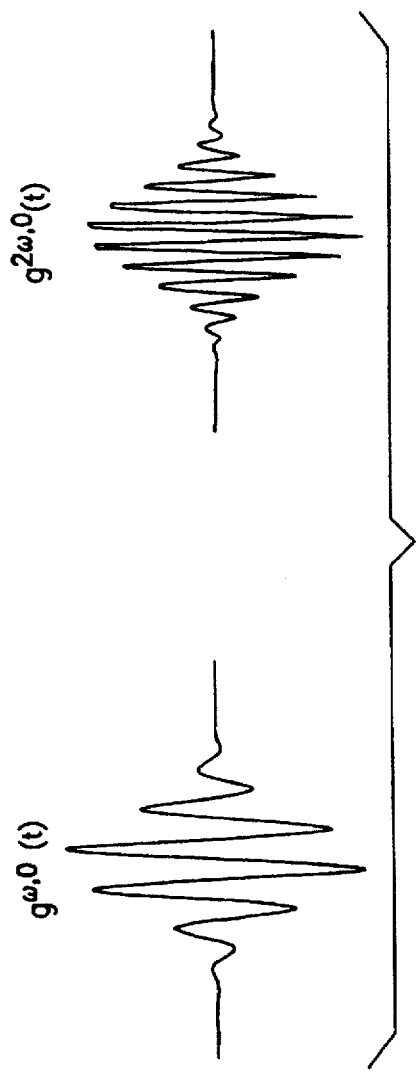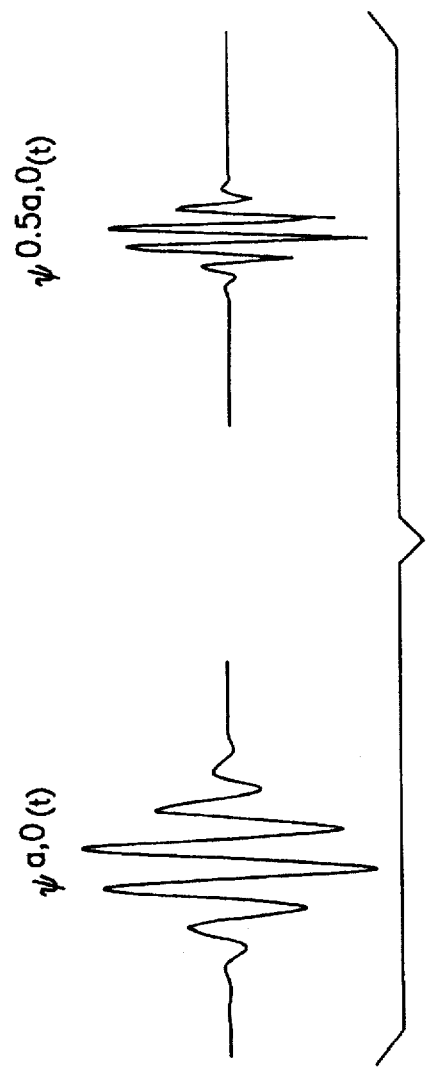

WAVELET ANALYSIS FOR LASER ULTRASONIC MEASUREMENT OF MATERIAL PROPERTIES

FIELD OF THE INVENTION

This invention relates generally to non-destructive materials characterization systems and methods and, in particular, relates to methods and apparatus for determining at least one property of a material using a laser ultrasonic approach.

BACKGROUND OF THE INVENTION:

Many types of materials processing require real-time monitoring of physical characteristics such as, by example, temperature, material phase, case hardening depth, and thickness. Often the processing environment or motion of the material makes direct contact measurement impossible. Conventional remote techniques have typically relied on the radiative properties of the material, as is the case with optical pyrometry for temperature measurement. However, emissivity changes during processing, and reduced sensitivity at low temperatures, preclude the use of this technique in many application.

A more suitable method for remote sensing of material properties is laser ultrasonics, in which a short intense laser pulse (impulse beam) generates a sudden localized thermal expansion which subsequently launches ultrasonic waves through the material. The passage of the waves is detected a short distance away on the surface of the material by a probe beam from an interferometer, and the speed of the ultrasound waves is calculated from the time of flight. The velocity of the wave propagation depends on the elastic constants of the target material, and thus is a function of the material properties, such as temperature. The separation of the two optical beam paths (impulse and probe) can be relatively small, enabling only localized material properties to be evaluated and mapped. This technique has been used extensively for nondestructive evaluation (NDE) and materials characterization. Reference in this regard can be made to Hutchins, D. and Tam, A. C., "Pulsed Photoacoustic Materials Characterization", IEEE Transactions on Ultrasonics, Ferroelectrics, and Frequency Control, Vol. UFFC-33, No. 5, September 1986, pp. 429–449.

However, in some cases the broadband laser ultrasound generation results in a surface displacement that is a complex function of frequency dependent wave velocities, making accurate time-of-flight measurements difficult. This problem can be further compounded by the typically low signal to noise ratios.

A standard signal processing technique is Fourier analysis, which presumes that a given signal can be expressed as the superposition of a series of sine waves. Each sine wave component has a given frequency and amplitude, where the amplitude corresponds to the energy of the original signal which is contained within that frequency. Thus a plot of amplitude versus frequency can readily show the dominant frequencies. This signal processing is useful for identifying predominant frequencies in periodic signals over many cycles, but since it has poor time-frequency localization it does not readily accommodate the case of a short, transient signal as is found in most laser ultrasonics applications.

A representative, but not exhaustive, list of U.S. Patents in the laser ultrasonics and related technical areas include the following: U.S. Pat. No. 3,601,490, issued 8/24/71 to K. Erickson and entitled "Laser Interferometer"; U.S. Pat. No. 3,694,088, issued 9/26/72 to J. Gallagher et al. and entitled "Wavefront Measurement"; and U.S. Pat. No. 4,633,715, issued 1/6/87 to J. Monchalin and entitled "Laser Heterodyne Interferometric. Method and System for Measuring Ultrasonic Displacements".

Also of interest is U.S. Pat. No. 5,286,313, issued 2/15/94 to Thomas J. Schultz, Petros A. Kotidis (an inventor of the subject matter of this patent application), Jaime A. Woodroffe, and Peter S. Rostler. The preferred embodiment of the system described in this patent employs an XeCl impulse laser in combination with a Helium-Neon based polarizing interferometer to provide, by example, remote detection of a temperature of a workpiece.

OBJECTS OF THE INVENTION

It is a first object of this invention to provide an improved laser ultrasonics materials measurement system.

It is a second object of this invention to provide a laser ultrasonics system that employs wavelet analysis to accurately determine a material property of interest, such as temperature, thickness, surface properties, and coating thickness.

It is a further object of this invention to provide a laser ultrasonics system that employs wavelet analysis to accurately determine a temperature of a silicon wafer during thermal processing of the wafer.

SUMMARY OF THE INVENTION

The foregoing and other problems are overcome and the objects of the invention are realized by methods and apparatus in accordance with embodiments of this invention, wherein a laser ultrasonics technique is used to characterize a composite dispersive response signal from a sample under analysis, such as a semiconductor wafer. Rather than measuring individual acoustic wave velocities at specific frequencies, an entire dispersive response signal is analyzed. In a presently preferred embodiment of this invention the entire dispersive response signal is analyzed using a wavelet-based technique, such as a discrete wavelet transform analysis technique. The discrete wavelet transform analysis technique is shown to provide an accurate, non-contact measurement of the temperature of the wafer.

It is shown that the discrete wavelet transform captures information expressive of the overall pattern of a signal, and therefore quantifies more than just the time of flight of the ultrasound signal. For example, if there is a change in the relative amplitudes of the ultrasound signal at two different frequencies, indicating a shift in the input energy distribution to the two frequencies, the times of flight may remain the same. Wavelet analysis, however, is shown to indicate the redistribution of the energy, which is indicative of a change in material properties, such as temperature.

BRIEF DESCRIPTION OF THE DRAWINGS

The above set forth and other features of the invention are made more apparent in the ensuing Detailed Description of the Invention when read in conjunction with the attached Drawings, wherein:

FIG. 4a illustrates windowed Fourier transform basis functions and FIG. 4b illustrates wavelet transform basis functions, FIGS. 4a and 4b providing a comparison of the two basis functions as the frequency is doubled;

DETAILED DESCRIPTION OF THE INVENTION

Figure 1:
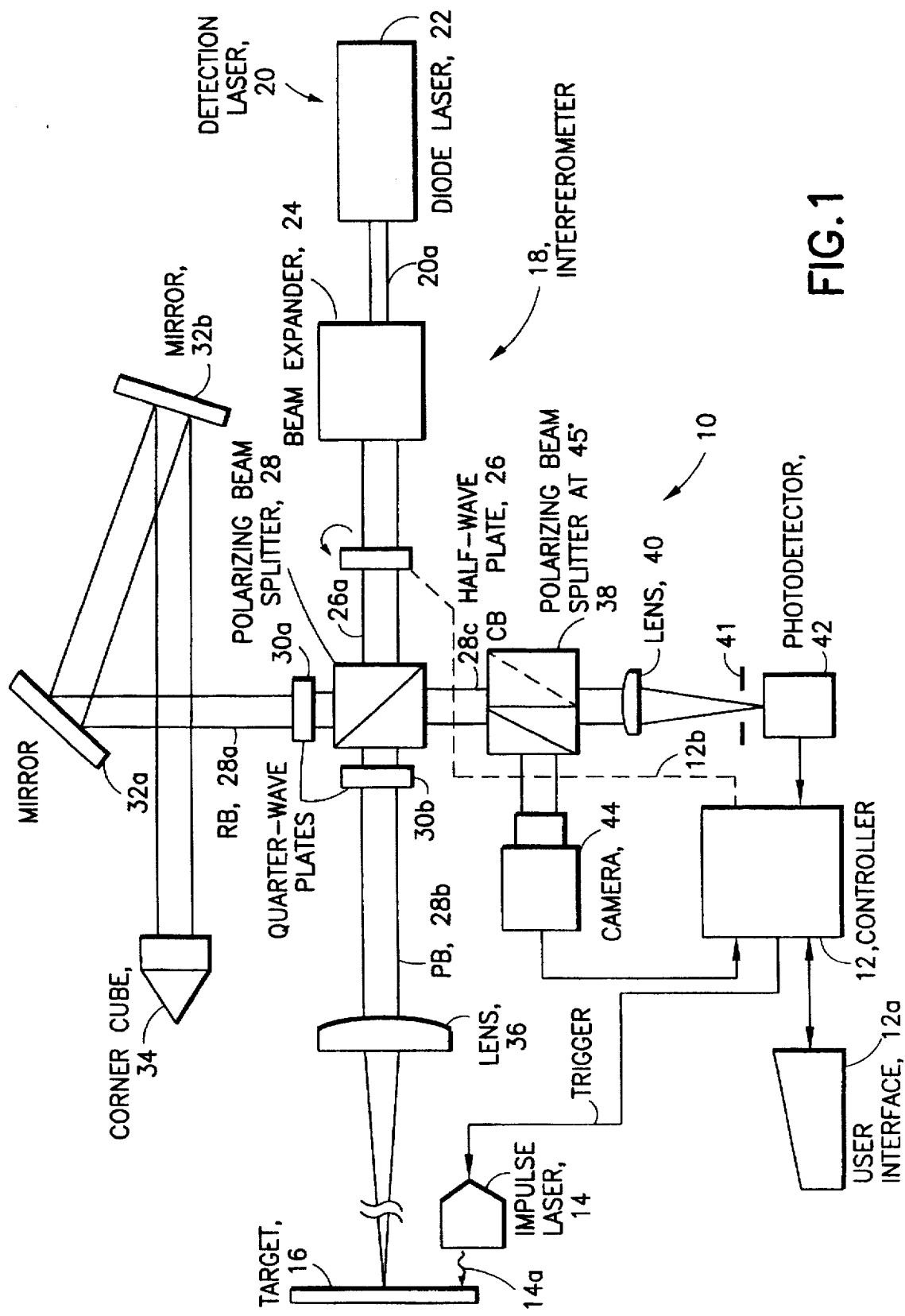
FIG. 1 is a block diagram of a presently preferred embodiment of a laser ultrasonics materials characterizing system.

FIG. 1 is a block diagram of a presently preferred embodiment of a laser ultrasonics materials analysis system 10 that is constructed and operated in accordance with this invention. The system 10 generally operates by launching an elastic wave within a target, sensing a varying surface displacement of the target due to the elastic wave, and then correlating the sensed displacement with a value of a property or properties of interest. As employed herein an elastic wave is intended to also encompass an acoustic wave. Also as employed herein a target may be a solid, a semi-solid, or a liquid.

A system controller 12, such as an embedded microprocessor or an externally connected computer or workstation, includes a user interface 12a that includes, by example, a touchscreen and/or a conventional keyboard and/or a pointing device (e.g., mouse) in combination with a graphical display device through which a user is enabled to interact and direct the operation of the system 10. An impulse laser 14 is controlled by the controller 14 to provide an impulse beam 14a to the surface of an object, hereafter referred to as a target 16 (the target forms no part of the system 10, and is shown only for completeness). The impulse beam 14a causes a localized heating of the target 16 and launches an elastic wave within the target as described previously. A displacement of the surface of the target 16 due to the elastic wave is detected by a polarizing interferometer 18, and the detected displacement is analyzed in accordance with a wavelet analysis technique, described in detail below, in accordance with this invention.

The interferometer 18 includes a detection laser assembly 20 which comprises a suitable laser 22, by example, a He-Ne laser, a Nd:YAG laser, an argon laser, or a diode laser. The selection of a particular laser 22 for use in the system 10 is a function of the required power, coherence length, wavelength, system compactness, and cost. Included with the detection laser 20 can be a conventional Faraday rotator (not shown) to prevent any reflected laser light that returns from the target 16 from effecting the performance of the laser 22. The output of the detection laser assembly 20 is a source beam 20a.

The source beam 20a is provided to a beam expander 24. The characteristics of the beam expander 24 directly impact the light collecting power of the sensor system described below. In general, the larger the beam diameter, the larger the return speckle size, and thus the greater is the fraction of the total returned power that is available to interference signal generation.

The beam expander 24 can be placed either before or after a polarizing beam splitter 28 that is described below. Placing the beam expander 24 after the beam splitter 28 has the advantage that the interferometer optics can be made smaller and also independent of the expansion ratio of the beam expander 24. However, placing the beam expander 24 at this position requires that the detection or probe beam (PB) 28b pass through the beam expander 24 twice. As a result, the quality (cost) and alignment of the beam expander 24 becomes important to the overall operation of the system 10. As such, and although it is preferred to place the beam expander 24 before the polarizing beam splitter 28, as illustrated in FIG. 1, the teaching of this invention is not so limited.

The expanded source beam 24a next encounters a half-wave plate 26 that is located before the polarizing beam splitter 28. The halfwave plate 26 provides a mechanism for setting a desired ratio for a reference beam (RB 28a) to probe beam (PB 28b) intensity. Varying the rotation angle of the halfwave plate 26 rotates the polarization of the laser beam and, in combination with the operation of the polarizing beam splitter 28 that is described next, thereby controls the fraction of the beam going into the PB 28b and into the RB 28a of the interferometer 18.

The halfwave plate 26 may be coupled to a mechanism, such as a motor, for imparting a rotary motion to the halfwave plate 26. In this embodiment the controller 12 automatically monitors the signal returned from the target 16 and controllably rotates the halfwave plate 26, via signal line 12b, so as to optimize the relative intensities of the reference and probe beams. Alternately, this function can be performed by a user who monitors a graphical display provided by a camera 44 (described below).

The rotated beam 26a that passes through the halfwave plate 26 is split into the RB 28a and PB 28b by the polarizing beam splitter 28, with the RB 28a and PB 28b having relative intensities set by the rotation imparted by the halfwave plate 26. After the reference and probe beams 28a and 28b leave the polarizing beam splitter 28 each passes through an associated ¼ wave retardation plate 30a and 30b, respectively. Plates 30a and 30b are aligned so that both of the RB 28a and PB 28b are circularly polarized.

The path length of the RB 28a is adjusted to reduce the noise in the signal that is detected from a combined beam (CB) 28c. The degree to which the lengths of the probe leg and the reference leg are matched is a function of the bandwidth of the laser 22, the fraction of the signal noise that is attributed to any frequency jitter of the laser 22, and the impact of the length of the reference leg on the overall compactness of the interferometer 18.

Included within the RB 28a leg are a plurality of folding mirrors 32a and 32b and a corner cube reflector 34. It is important to the operation of the interferometer 18 that the reference leg return beam be at the same angle (opposite direction) as the outgoing reference beam. This important goal is achieved in a simple, compact, and inexpensive manner using the corner cube 34. In contrast, a simple mirror would require careful and precise adjustment, and very high quality mounts all along the reference path to maintain the alignment. In the presently preferred embodiment of this invention these requirements are eliminated by the use of the corner cube 34 (preferably gold coated and hollow) which terminates the reference beam path leg while preserving the polarization characteristics of the RB 28a.

The PB 28b is focussed to a point on the target 16 using a lens 36 that has a focal length equal to the distance to the target 16. That portion of the PB 28b that reflects from the surface of the target 16 is subsequently collimated by the lens 36 as it travels back into the interferometer 18.

The same prism (the polarizing beam splitter 28) that is used to split the polarized beam 26a into the RB 28a and the PB 28b is also is used to recombine the RB 28a and the returned (reflected) portion of the PB 28b into a combined beam (CB) 28c. Because the RB 28a and the PB 28b are circularly polarized, and must pass back through the ¼ wave plates 30a and 30b, respectively, they are again linearly polarized, but at the opposite orientation than their original linear polarizations. Because of this, the CB 28c does not go back toward the laser 22, but instead is directed into a signal detection portion of the interferometer 18.

As was stated, after the RB 28a and the PB 28b are combined they are both linearly polarized, but of the opposite sense. In order to generate an interference signal (detectable interference fringes), a polarizing prism or beam splitter 38 oriented at 45° is used to select a projection of the polarization axis of each of the RB 28a and the PB 28b along a common axis. This results in two combined beams whose interference signal is 180° out of phase. Either or both of these beams can be used to provide the signal necessary for process analysis. For example, two photodetectors can be used for detecting two combined beams. A combined beam focussing lens 40 is used to focus the CB(s) 28c onto a radiation sensitive surface of one or more photodetectors 42. The lens 38, in combination with an aperture 41, can also be used to spatially block out light other than that of the combined beams from impinging on the photodetector 42.

The photodetector 42 may be provided in a number of suitable forms, depending on performance characteristics. Both conventional photomultiplier tubes and hybrid photodiode/amplifiers are suitable embodiments for detecting the light and dark pattern that results from the interference of the RB 28a and the returned portion of the PB 28b within the CB 28c. The output of the detector 42 is provided to the controller 12 for wavelet analysis signal processing in the manner described below.

An optional camera 44 is primarily used as a diagnostic tool, i.e., the camera 44 useful for optimizing the detected signal when an operator is setting up and controlling the system 10. For example the camera 44, which may be a conventional CCD device that provides an output to a display monitor of the user interface 12a, provides visual feedback to the operator for best signal return, which implies a best pointing angle to the target 16. However, an automatic beam steering system can also perform this function without operator intervention. The camera 44 may also be used for alignment of the signal and reference beams. The camera 44 can also be employed to determine the relative intensity of the reference and signal beams and, based on the indicated intensities, the operator is enabled to rotate the halfwave plate 26 to achieve an optimum intensity distribution for optimum fringe contrast.

It should be realized that if the camera 44 is eliminated a second photodiode can be installed in its place. The use of a second photodiode enables a square and add signal processing technique to be used, as described in the above-referenced U.S. Pat. No. 5,286,313.

Figure 2:
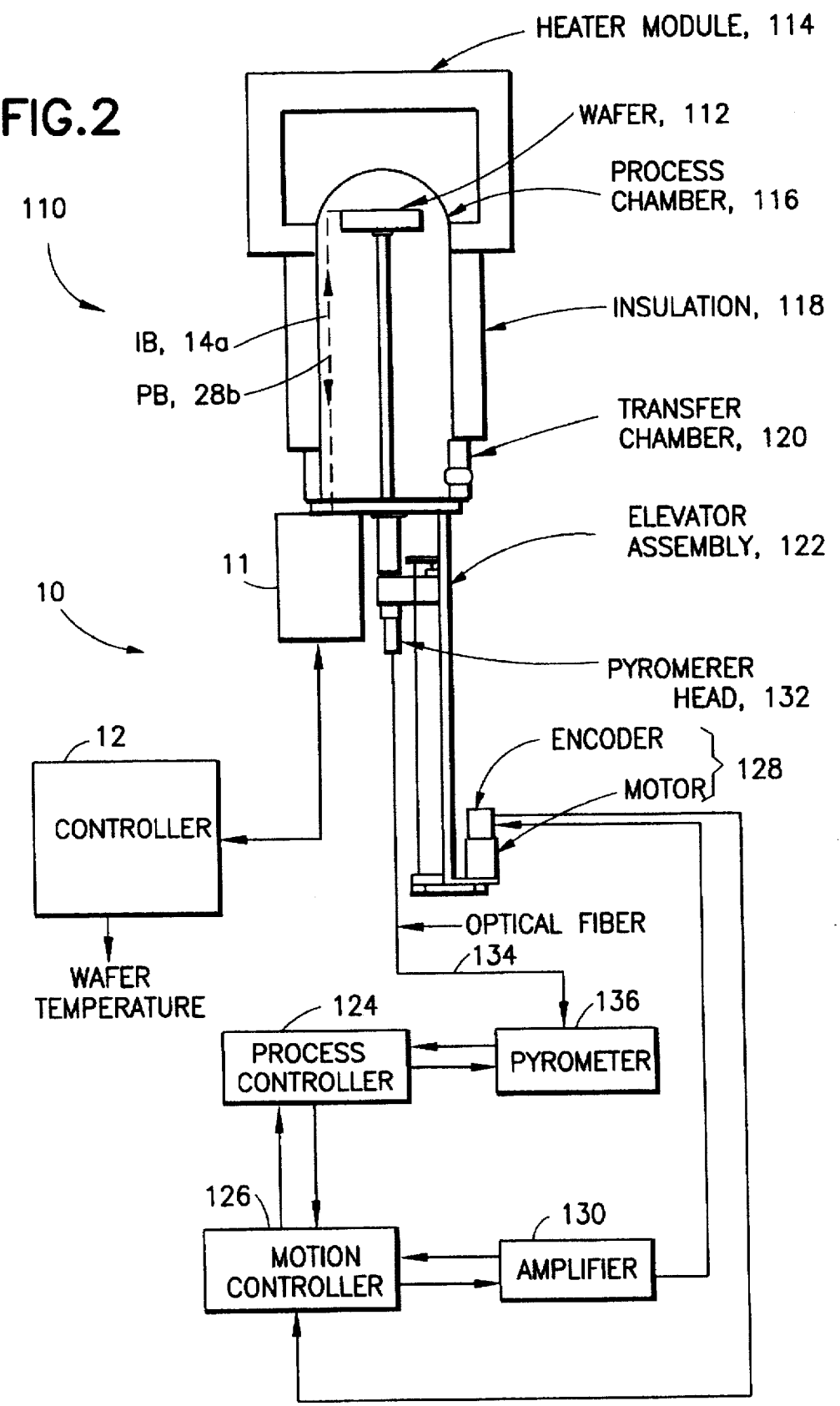
FIG. 2 is a cross-sectional view, partly in block diagram form, of a rapid thermal processing (RTP) system that is constructed and operated in accordance with this invention.

An application of the system 10, and in particular the novel wavelet processing technique of this invention, is illustrated in FIG. 2. This figure generally shows a rapid thermal processing (RTP) system 110 which is used for the thermal processing of a silicon wafer 112. A heater module 114 surrounds a portion of a process chamber 116 which is covered by a layer of thermal insulation 118. A lower transfer chamber 120 enables the wafer 112 to be loaded into and extracted from the process chamber 116. After being loaded an elevator assembly 122 is used to raise and lower the wafer 112 within the process chamber 116. A very rapid heating (e.g., 50°-100°/sec) of the wafer 112 occurs during this process. Also shown in FIG. 2 are various other system components such as a process controller 124, an elevation motion controller 126, and an associated motor/encoder 128 and amplifier 130 for raising and lowering the elevator assembly 122. A pyrometer head 132 is connected via an optical fiber 134 to a pyrometer 136 for measuring, by emissivity, the temperature within the process chamber 116. The pyrometer 136 is interfaced to the process controller 124 to close the temperature control loop.

In accordance with the invention the RTP system further includes the laser ultrasonics materials analysis system 10 of this invention that employs wavelet transform analysis processing. A laser head 11 is disposed so as to direct the impulse beam 14a and the probe beam 28b onto a surface of the wafer 112 during the thermal processing of the wafer.

The temperature measurement of the wafer 112 occurs without using the emissivity of the silicon wafer, which would be difficult to accurately measure within the high ambient temperature of the process chamber 116.

This is an important application of the invention as it avoids processing errors which can result in the destruction of the wafer 112. As larger wafers come into use (e.g., 8" to 12" wafers) the expense of a single wafer, which may have a very significant production cost associated therewith, makes an accurate measurement of wafer temperature an important goal.

Having thus described an embodiment of a laser ultrasonics system that is suitable for use in practicing this invention, and having also described one important but not limiting application of the invention, a detailed description is now made of the wavelet analysis processing technique, in accordance with this invention, for determining a characteristic, such as temperature, of a material, such as the wafer 112 of FIG. 2.

The deficiencies of the conventional Fourier analysis signal processing technique, when applied to short duration, transient signals, was discussed previously.

These deficiencies can be at least partially overcome for transient signals by processing with a windowed Fourier transform. In this case, the basis function is a sine wave which is localized within a decaying envelope that is moved in the time domain. The presence of higher frequencies simply produce more cycles within the same envelope. It can be shown mathematically that since the window is fixed, so are the time and frequency resolutions of this technique. Limitations arise when the signal has both high and low frequency components, where it is desirable to have better time resolution at the higher frequencies.

This limitation can be overcome by using as basis functions those which can be both translated and dilated. Such window functions, denoted as affine wavelets or herein simply as wavelets, have the special property that they provide improved frequency resolution at low frequencies, and improved time resolution at high frequencies.

In wavelet analysis, a class of functions denoted as a "mother wavelet" is selected as the basis for decomposition of the subject transient signal. Each single basis function, or wavelet, is a translated and/or dilated version of other wavelets, with the amplitude modulated to maintain the total energy constant. If the entire series of translated and dilated wavelets are transformed, the result is a series of unit vectors forming a complete basis. A wavelet can be visualized, therefore, by running a unit vector through an inverse wavelet transformation.

Figure 3A:
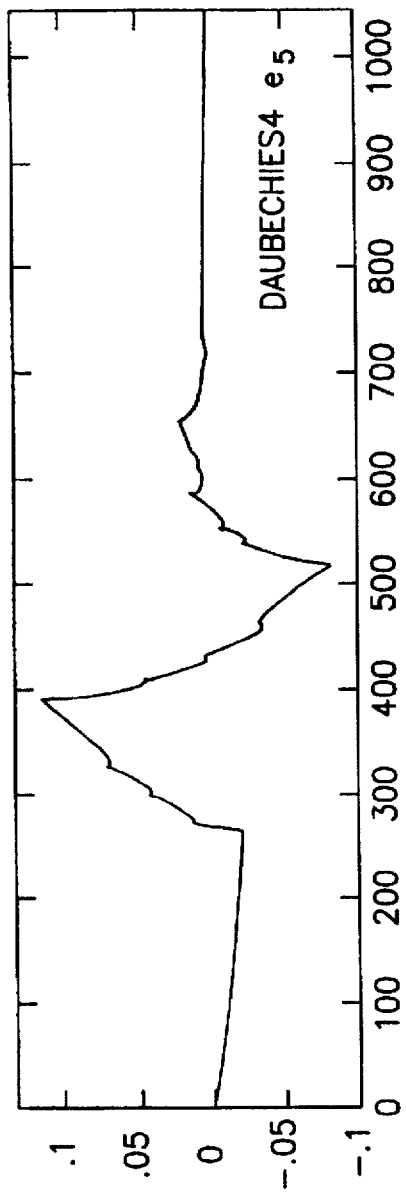
FIGS. 3a and 3b illustrate two graphs showing exemplary Daubachies wavelet functions, the graphs being useful in explaining the wavelet analysis technique that is a feature of this invention.
Figure 3B:
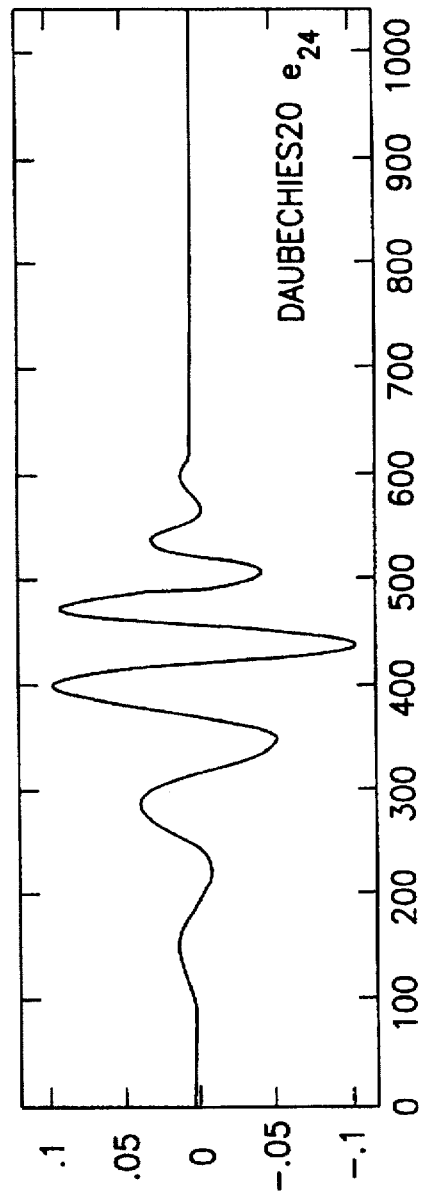

FIGS. 3a and 3b show wavelets generated in this manner for two typical mother wavelet families: i.e., the Daubechies4 and Daubechies20 families. Reference in this regard can be had to Daubechies, I., *Ten Lectures on Wavelets*, Society for Industrial and Applied Mathematics, Philadelphia, Pa., 1992, pp. 10–16.

The Daubechies4 wavelet of FIG. 3a was generated by a unit vector in the 5th of 1024 components, while the Daubechies20 wavelet of FIG. 3b was produced by a unit vector in the 24th of 1024 components. Note that while a wavelet function is continuous, it is not necessarily differentiable everywhere, as seen in the Daubechies4 function. However, wavelets can still exactly recreate some smooth functions.

The fact that a wavelet function can be compressed in the time domain gives rise to the increased time resolution at high frequency. FIGS. 4a and 4b show a comparison of windowed Fourier transform basis functions and wavelet transform basis functions, respectively, at increasing frequency. In particular, the waveforms on the right are doubled in frequency over those on the left. As is apparent, for the Fourier transform case (FIG. 4a) the duration of the envelope remains the same while the number of signal excursions doubles, while for the wavelet transform case (FIG. 4b) the duration of the envelope is decreased by a factor of two, while the number of signal excursions remains the same. Reference in this regard may be had to Livstone, M. M., "Wavelets: A Conceptual Overview", MIT Industrial Liaison Program Report 9-26-94, Massachusetts Institute of Technology, Cambridge, Mass., pp. 3–4.

One tradeoff in wavelet analysis is that time dilations of the wavelets at higher frequencies reduces the frequency resolution, and vice versa. However, this may be an acceptable compromise because short duration, low frequency signals often cannot be well localized in the time domain. As a result, in this case good frequency resolution is more desirable than good temporal resolution. Conversely, high frequency transients can be located accurately in time, thereby making transient event detection feasible.

Wavelet transforms may be considered as either continuous or discrete. In the continuous wavelet transform, the parameters which control the translation and dilation vary continuously over all real numbers. For discrete wavelet transforms, these parameters take only discrete values which, if chosen correctly, provide orthonormal wavelet bases. The Discrete Wavelet Transform (DWT) allows rapid computational techniques, similar in speed to the Fast Fourier Transform, to be employed in decomposing a signal into the superposition of wavelets with discrete time dilation and translation constants. The results may be expressed as a phase-plane map in which time and frequency form the axes. The coefficient for each wavelet occupies a certain range of position and frequency corresponding to the resolutions of each parameter, producing a rectangular area on the map. Constant wavelet energy considerations dictate that the position and frequency resolutions are inversely proportional for wavelet transforms. Thus, if the frequency is very narrow (i.e., well-known), the position must be broad, and vice-versa.

A third factor for each set of translation and dilation parameters is also generated for representing the fraction of energy of the original signal contained within a particular wavelet. This third factor can be denoted by a shading of the time-frequency domain on the two-dimensional phase-plane map.

Figure 5:
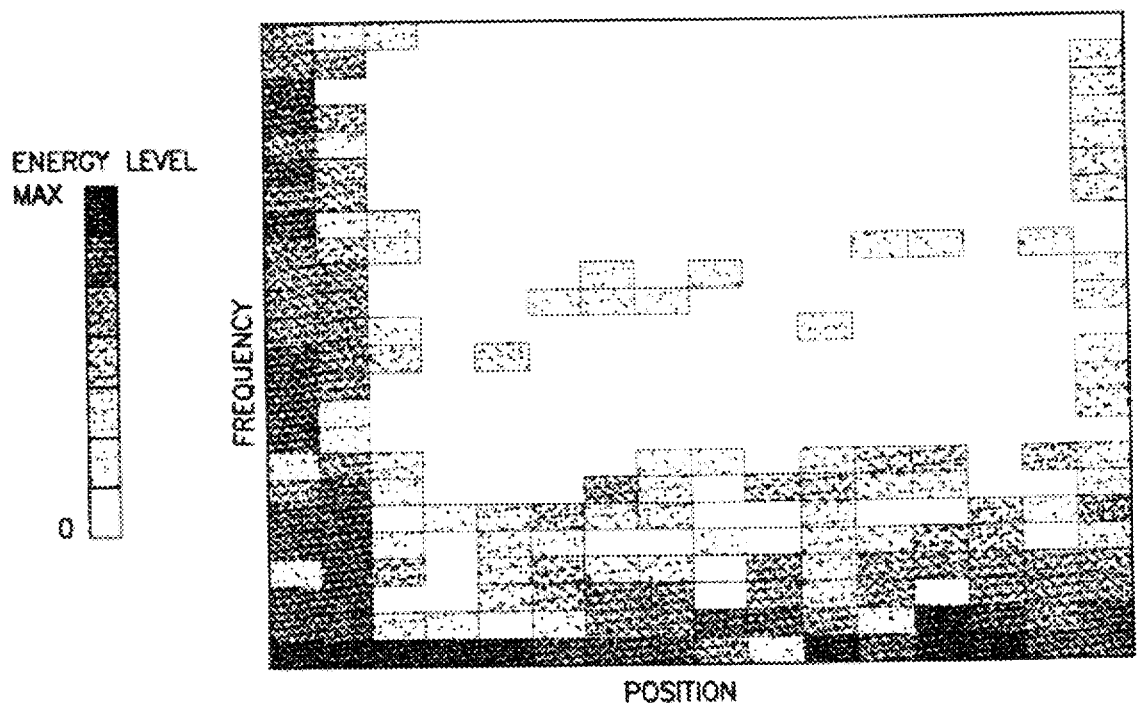
FIG. 5 is a phase-plane representation of a wavelet transformed signal with uniform frequency and position intervals.
Figure 6:
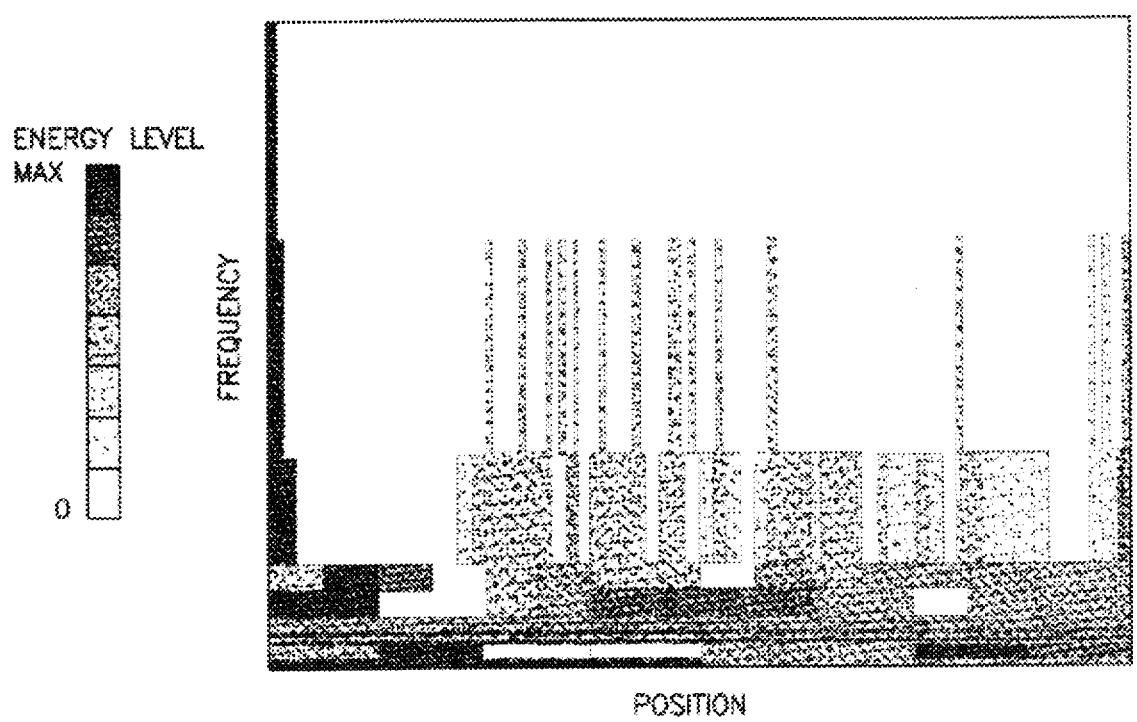
FIG. 6 is a phase-plane representation of a wavelet transformed signal with optimal frequency and position intervals.

FIG. 5 shows the phase-plane map for a typical transient signal at a fixed dilation constant using the Daubechies4 mother wavelets, while FIG. 6 shows an optimal phase-plane map for the same signal. It should be noted that in FIG. 6 the time-frequency increments differ from those shown in FIG. 5 because the combination of translated and dilated versions of the mother wavelet, which best reproduces the original signal, has been selected (thus optimizing the phase-plane map). This set of (optimum) coefficients is known as the best basis. The phase-plane map of FIG. 6 shows clearly how the Discrete Wavelet Transform provides for multiscale analysis.

From FIG. 6, it can further be noted that most of the energy of the measured trace is contained within just a few coefficients. This means that virtually all of the information of the original signal can be stored or transmitted by relatively little data and, so long as the mother wavelet family is known, the signal can be easily reconstructed. The Discrete Wavelet Transform further allows the wavelet coefficients to be used as figures of merit for a given signal.

Having described the Discrete Wavelet Transform Analysis technique in a general manner, the application of the DWT Analysis technique to ultrasonic signals is now described in detail.

Figure 7:
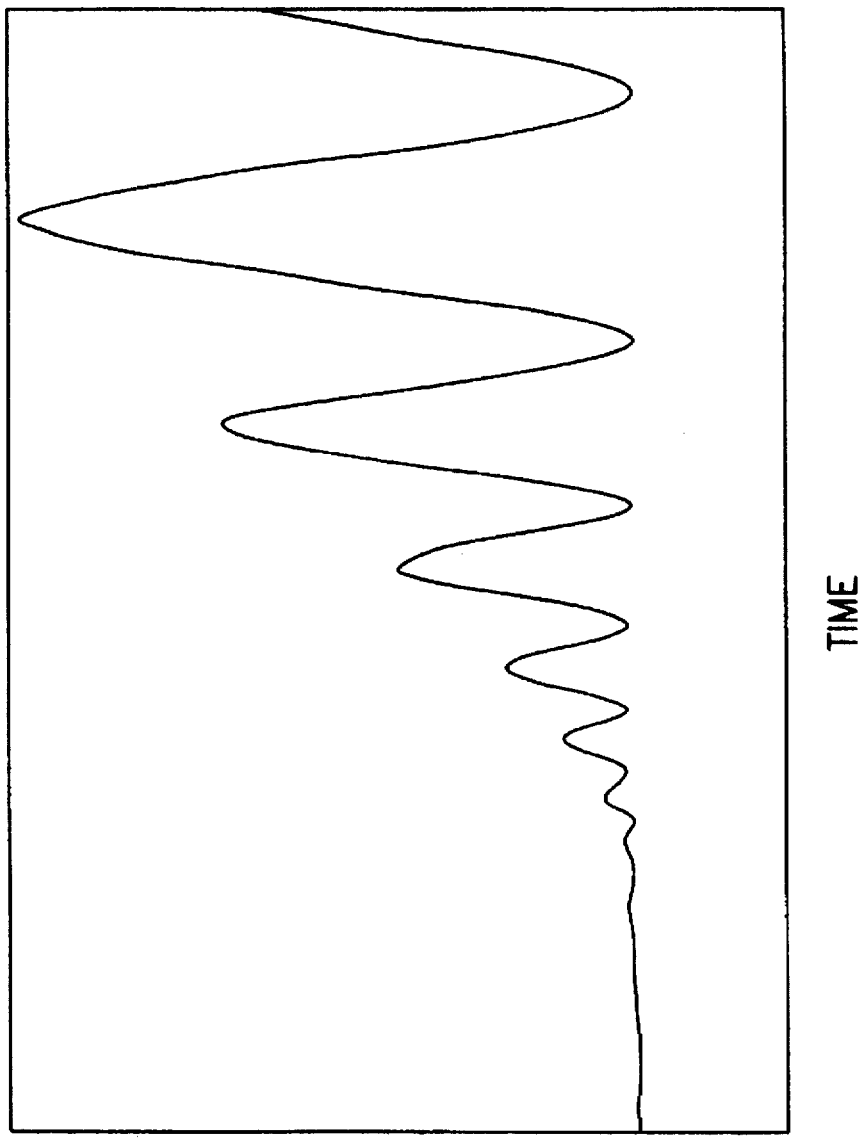
FIG. 7 is a graph illustrating a leading edge of a typical ultrasound signal that is generated in a silicon wafer by the system shown in FIGS. 1 and 2.

When an ultrasonic response is generated in a material, the measured signal, typically surface displacement, exhibits transient behavior with a few oscillations that eventually decay to zero. In certain cases, these oscillations are highly dispersive in the range of frequencies generated by laser ultrasound. FIG. 7 shows a leading edge of a typical laser-induced ultrasonic signal generated in a silicon wafer, such as the wafer 112 illustrated in FIG. 2.

The inventors have realized that since the ultrasound generation clearly defines the start time of the signal, and since there are few oscillations at any given frequency, the ultrasound signal forms a suitable candidate for wavelet analysis.

One benefit in using wavelet analysis on an ultrasound signal is that a significant amount of information about the signal is captured in a few dominant wavelet coefficients. This feature is extremely useful when analyzing several different ultrasound signals which vary only slightly from one another, as would be the case if the ultrasound were generated in a material with properties that varied as the signals were being captured. Such changes in frequency content are difficult to detect since there are so few cycles to work with, and shifts in the time domain can be small enough that they cannot be reliably measured. Since wavelet analysis captures information about the overall pattern of a signal, changes from signal to signal that are difficult to resolve in the time domain are measurable in the transformed phase-plane space of a type illustrated in FIGS. 5 and 6.

EXAMPLE

The use of wavelet analysis for remote sensing of material properties was performed using a laser ultrasound system similar to that illustrated in FIGS. 1 and 2. The target of interest was a silicon semiconductor wafer, such as the wafer 112 shown in FIG. 2. Temperature was selected as the property of interest, although the teaching of this invention is not limited only to the determination of temperature. A sample wafer was heated in a furnace between room temperature and 1000° F., and a reference temperature measurement was provided by a thermocouple. Interferometric signals output from the system 10 were digitized and recorded. For each trace, 100 ultrasound signal events were acquired, squared to eliminate interferometer phase artifacts, and averaged to produce the final ultrasonic signal or trace. Each trace consisted of 1024 data points taken over a 10 μsec interval, starting 3 μsec after the impulse laser 14 was triggered. A commercially available wavelet analysis program was used to analyze the traces, specifically one known as Wavelet Packet Laboratory Software, Version 1.02, available from Digital Diagnostic Corporation of Hamden, Conn.. The teaching and practice of this invention is not, however, limited only to the use of this one commercially available wavelet software package.

The signals were processed using the same mother wavelet, in this case the Vaidyanathan24 function. This function was empirically chosen from among a number of suitable other classes of mother wavelets. The selection was based on the processing and subsequent qualitative observation of wavelet coefficients for a representative laser ultrasonics signal. Functions of various classes were tested, and the chosen function was deemed to concentrate the signal energy within a minimum number of coefficients at each dilation level. Similarly, a constant dilation parameter was chosen which best represented the sample signals, as indicated by the localization of the total signal energy within the fewest wavelet coefficients at that level of analysis. It should be noted that the best basis combination of translation and dilation parameters was not used because the combination could change from signal to signal and, therefore, a given coefficient could not necessarily be used for consistent comparison.

Observing the coefficients from the seventh-level analysis, where the wavelets were dilated in time by ($\frac{1}{2}^7$) of the mother wavelet, the energy content of the largest coefficient was recorded for the first signal and compared to the values for that same coefficient with each subsequently analyzed signal (see FIG. 9). The variation of this coefficient with temperature, corresponding to the variation of the fractional signal energy contained within that particular wavelet, was found to be approximately an order of magnitude larger than any measurable variation in the time domain.

Figure 9:
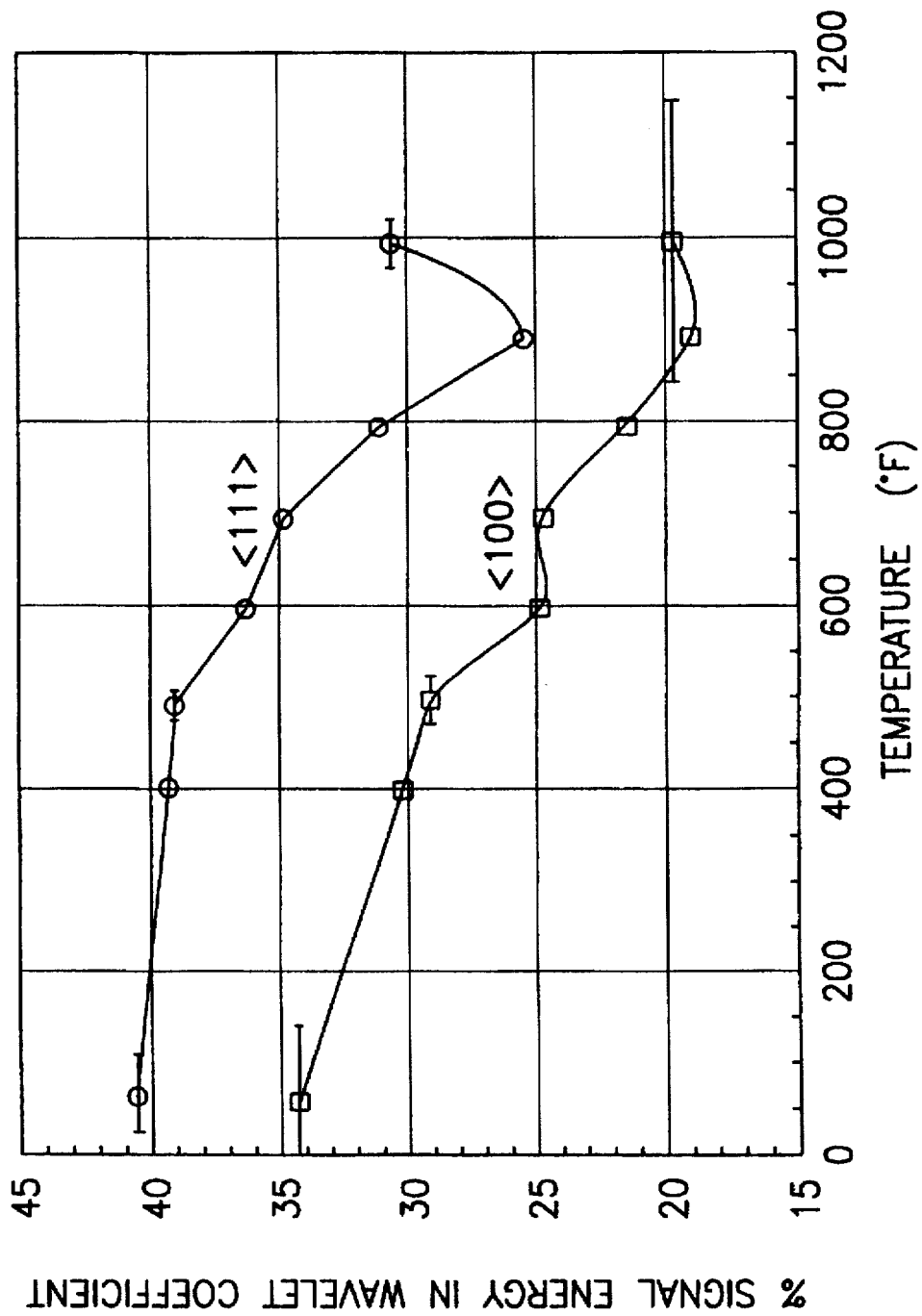
FIG. 9 illustrates, in accordance with this invention, the results of wavelet analysis for the silicon wafer ultrasound data shown in FIG. 8 for the <111> silicon wafer, and also the results of wavelet analysis for a <100> silicon wafer.

That is, the energy found in at least one coefficient of the wavelet is correlated with a property of interest of the wafer, such as temperature, as will be shown in FIG. 9.

Other beneficial features of this technique are that lower levels of signal-to-noise can be tolerated, because the time-frequency localization can be tuned. That is, since the technique analyzes the entire pattern of the signal and can be locally optimized, relevant features can be identified even with spurious information elsewhere in the signal. For example, event detection can be accomplished by increasing resolution in time preferentially for the portion of the signal where the transient occurred. Other portions of the signal could be optimized differently in the time-frequency mapping to minimize the effect of that noise and at the same time gain additional information about the overall signal's features. Furthermore, the results are already normalized, since it is the fractional energy that is being measured. These properties are particularly desirable for a laser ultrasonics application where the energy deposition into specific ultrasonic frequencies cannot be readily controlled.

Figure 8:
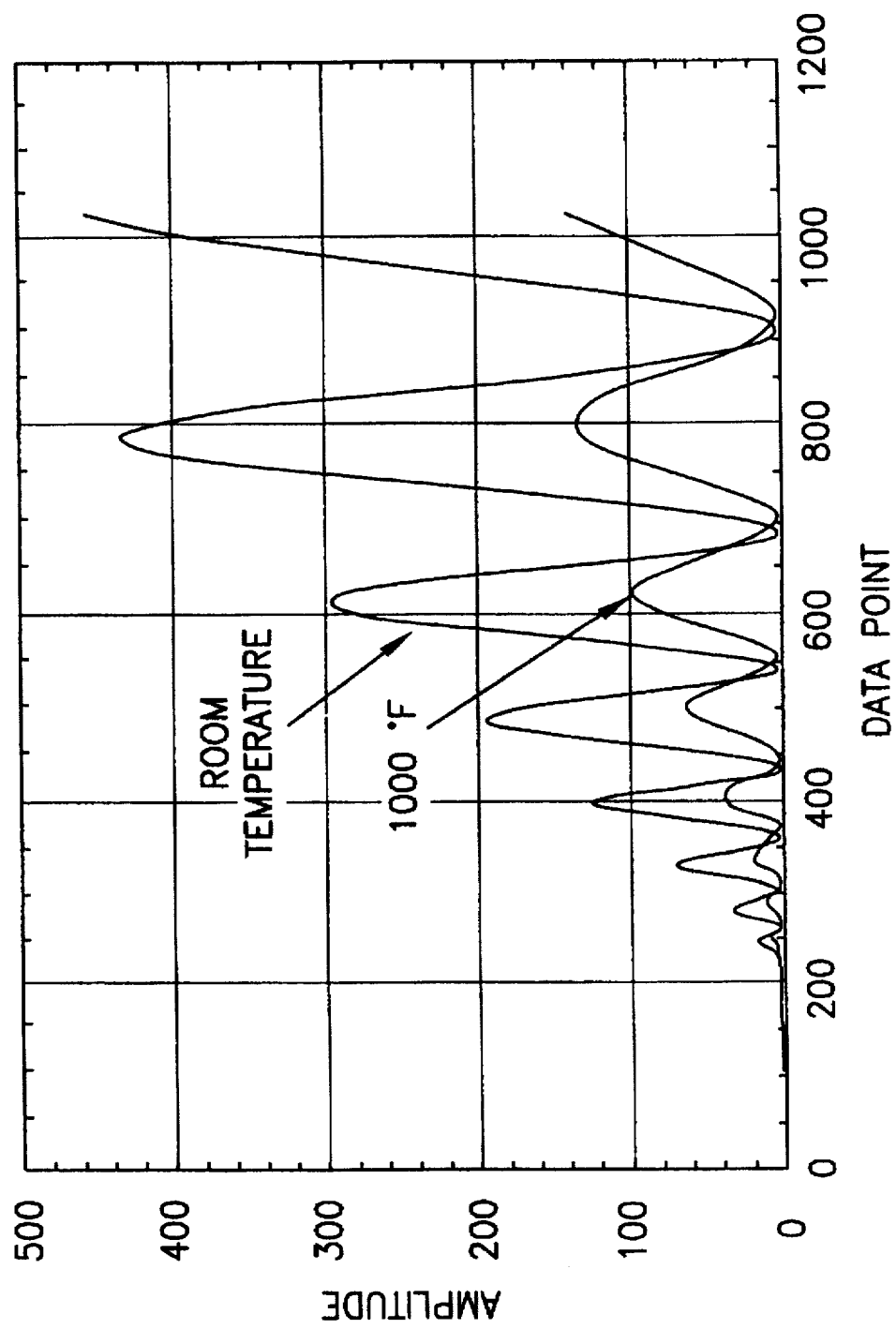
FIG. 8 is a graph showing squared and averaged ultrasound signals taken at two different temperatures for a <111> silicon wafer.

Both theory and experimental data show that, for the apparatus being used, a temperature resolution of about 10° F. requires a resolution of 5 nanoseconds in conventional time of flight measurements (signal-to-signal). However, both noise and sample rate issues make this degree of temporal resolution between signals difficult to achieve. By example, FIG. 8 shows typical squared and averaged ultrasound signals taken at 68° F. and 1000° F. for a <111> silicon wafer. The variation in amplitude with time (expressed in sampling points) indicates that there is relatively little shift in the time domain of the ultrasound response over this wide temperature range.

However, when the same data is analyzed using the wavelet technique described above, the changes with temperature are readily measured. In this regard FIG. 9 is a plot of the energy content of the peak wavelet coefficient, at the seventh level, versus temperature for the <111> silicon wafer plotted in FIG. 8. A monotonic decrease occurs between room temperature and about 900° F., indicating a sudden change in material properties at that temperature. Accuracy of the temperature measurements in the region of primary interest, between about 400° F. and 900° F., was found to average approximately ±20° F. This level of accuracy resulted from the sample rate of the data acquisition system recording the ultrasound trace. The uncertainty in temperature measurement decreases when the sample rate is increased. The measurements taken from a <100> silicon wafer are also shown in FIG. 9.

From FIG. 9 it can be realized that not only can the temperature be characterized but, assuming that temperature was known a priori, some other material property of a sample can be determined using the wavelet analysis technique. By example, FIG. 9 makes it clear that one or more properties characteristic of the sample's material structure (e.g., presence of lattice defects, doping level, or some other parameter affecting the elastic constants other than temperature) can be identified and distinguished.

Based on the foregoing it can be appreciated that wavelet analysis can be employed to process laser ultrasound signals obtained from a target with varying material properties, such as temperature and crystal structure. The technique is also applicable to the measurement of other material properties and structure-related characteristics, such as case depth, the ratio of austenite to martensite (as well as other phase changes), and also thickness. By measuring the energy content of at least one particular wavelet coefficient for each signal processed with Discrete Wavelet Transforms, a basis of comparison among the signals is obtained which has a greatly improved resolution over comparisons made only in the time domain (e.g., time-of-flight).

Furthermore, the laser ultrasonics wavelet analysis technique in accordance with this invention can be used with signals with relatively poor signal-to-noise ratios, since it captures information about the overall pattern of the signal, and is independent of the absolute amplitude of the signals.

The teaching of this invention is not limited to only the examples given above. For example, the laser ultrasonics wavelet analysis technique of this invention can be used for the measurement of surface properties. This is an application wherein there is a modification of the surface properties by some kind of surface treatment. The result is a gradient of a particular material property from the surface to the bulk of the material. An example of such a process is the diffusion of carbon into steel during carburization. The result is a surface hardened material with carbon on the surface. The process is usually called case hardening, and the depth of carbon penetration is referred to as case depth. In some cases, the case depth can be quite large, i.e., up to 0.25" and the carbon gradient can start at high levels on the surface, for example 5–10%, and drop to about 2% in the bulk. The system 10 of FIG. 1 can be used to measure the depth of the surface layer by analyzing the dispersion of the ultrasonic waves using wavelets.

In a further application the system 10 can be used to measure surface coatings. In this application, the system 10 measures the properties of coatings, e.g., thickness, integrity, uniformity, etc. This technique is similar to the technique described immediately above, and differs most significantly in that in this case there is a clear and sharp interface between the coating and the substrate. This method applies to any kind of coating, e.g., metal-on-metal, paint-on-paint, paint-on-plastic, etc., so long as an interface exists between a coating and another coating or the bulk. In addition, the coating thickness can range from microns to several millimeters or more. The frequency of the ultrasonic wave can be adjusted according to the thickness of the coating, e.g., higher frequency for thinner coatings. Such frequency control can be achieved by controlling the thickness of the impulse beam ring on the target.

The system 10 using wavelet analysis is applicable to both on-line and post-processing Control. An example of on-line control is the galvanization of steel, where zinc is deposited on the surface of a thin strip. Measurement and control of the properties and thickness of the zinc coating are critical, and are accurately obtained in accordance with the teachings of this invention.

While the invention has been particularly shown and described with respect to preferred embodiments thereof, it will be understood by those skilled in the art that changes in form and details may be made therein without departing from the scope and spirit of the invention. By example, the teaching of this invention is not limited for use only with the particular polarizing interferometer as shown in FIG. 1, nor is it limited for use only with an impulse laser for generating the ultrasound signal, nor is it limited for use only with semiconductor wafers, or silicon semiconductor wafers in particular. That is, and by example, semiconductor wafers comprised of Group II–VI and Group III–V materials can be characterized as well using the teachings of this invention.

It should therefore be realized that the teaching of this invention should be given a scope commensurate with the scope of the claims that follow.

What is claimed is:

1. A system for determining a characteristic of a target, comprising:
    means for launching an elastic wave within the target;
    an interferometer for detecting a displacement of a surface of the target in response to said launched elastic wave;
    means, responsive to said detected displacement, for determining an amount of energy that is contained within at least one wavelet coefficient; and
    means for correlating the energy with a characteristic of the target.

2. A system as set forth in claim 1, wherein the target is a semiconductor wafer.

3. A system as set forth in claim 1, wherein the characteristic of the target is temperature.

4. A system as set forth in claim 1, wherein the characteristic of the target is at least one of structure, material properties, and thickness.

5. A method for remotely detecting a characteristic of a target, comprising the steps of:
    (a) interferometrically generating an oscillating signal that is indicative at least in part of a surface motion of the target;
    (b) detecting an amplitude and a frequency of the generated oscillating signal to generate a detected signal;
    (c) generating a set of processed data that includes the detected signal; and
    (d) analyzing the set of processed data with a discrete wavelet transform technique to determine the characteristic of the target.

6. A method as set forth in claim 5, wherein the target is a semiconductor wafer.

7. A method as set forth in claim 5, wherein the characteristic of the target is temperature.

8. A method as set forth in claim 5, wherein the characteristic of the target is at least one of structure, material properties, and thickness.

9. A system for determining a temperature of a semiconductor wafer, comprising:
    impulse means for generating an impulse beam and for directing said impulse beam to a surface of the wafer for launching an elastic wave within the wafer;
    interferometer means for detecting a displacement of the surface of the wafer in response to the launched elastic wave;
    discrete wavelet transform means for determining, from said detected displacement, a time varying characteristic of said elastic wave within the wafer; and
    means for correlating said determined time varying characteristic with the temperature of the wafer.

10. A system as set forth in claim 9, wherein said interferometer means includes a laser generating an output beam, means for directing a portion of said output beam to the surface of the wafer as a probe beam, means for generating a reference beam from a portion of said output beam, means for combining a portion of said probe beam reflecting from the surface of said wafer with said reference beam, and means for detecting the displacement as a function of a change in interference between said probe beam and said reference beam.

11. A method for determining a temperature of a semiconductor wafer, comprising the steps of:
    interferometrically generating an oscillatory electrical signal that is representative of a transient oscillation of a surface of the wafer;
    analyzing the electrical signal with a function that concentrates the electrical signal energy within a minimum number of wavelet coefficients at individual ones of a plurality of dilation levels; and
    determining the temperature of the wafer in accordance with the analyzed electrical signal.

12. A method as set forth in claim 5 wherein the set of processed data is generated by the steps of:
    repeating steps (a) and (b) a plurality of times to generate a plurality of detected signals; and
    squaring and combining the plurality of detected signals to generate the set of processed data.

* * * * *